US012697243B2

(12) United States Patent
Vossoughi

(10) Patent No.: US 12,697,243 B2
(45) Date of Patent: Aug. 4, 2026

(54) METHOD AND APPARATUS TO MAINTAIN DISTANCE BETWEEN BONES OF A BACK FOR PAIN RELIEF

(71) Applicant: Jafar Vossoughi, Brookeville, MD (US)

(72) Inventor: Jafar Vossoughi, Brookeville, MD (US)

(*) Notice: Subject to any disclaimer, the term of this patent is extended or adjusted under 35 U.S.C. 154(b) by 198 days.

(21) Appl. No.: 18/478,218

(22) Filed: Sep. 29, 2023

(65) Prior Publication Data

US 2025/0107901 A1    Apr. 3, 2025

(51) Int. Cl.
*A61F 5/058*        (2006.01)
*A61F 5/02*         (2006.01)
*A61F 5/055*        (2006.01)

(52) U.S. Cl.
CPC ............ *A61F 5/05883* (2013.01); *A61F 5/02* (2013.01); *A61F 5/055* (2013.01)

(58) Field of Classification Search
CPC .......... A61F 5/024; A61F 5/026; A61F 5/028; A61F 5/03; A61F 5/02; A61F 5/022; A61F 5/04; A61F 5/042; A61F 5/05; A61F 5/058; A61H 1/02; A61H 1/0218; A61H 1/0292
See application file for complete search history.

(56) References Cited

U.S. PATENT DOCUMENTS

| | | | |
|---|---|---|---|
| 1,577,712 A | | 3/1926 | Graham |
| 2,198,908 A | * | 4/1940 | Ellis ........................... A61F 5/04 |
| | | | 602/40 |
| 2,746,451 A | * | 5/1956 | Parker ....................... A61F 5/11 |
| | | | 403/44 |
| 3,957,040 A | | 5/1976 | Calabrese |
| 4,419,991 A | * | 12/1983 | Lee ........................ A61F 5/0585 |
| | | | 602/16 |
| 4,657,000 A | | 4/1987 | Hepburn |
| 4,907,575 A | * | 3/1990 | Satterthwaite .......... A61F 5/024 |
| | | | 602/19 |

(Continued)

FOREIGN PATENT DOCUMENTS

| | | | | |
|---|---|---|---|---|
| CN | 113081432 A | * | 7/2021 | ............. A61F 5/028 |
| KR | 20160068213 A | * | 6/2016 | ............. A61F 5/024 |

OTHER PUBLICATIONS

KR-20160068213 Machine Translation (Year: 2016).*
CN-113081432 MT (Year: 2025).*

*Primary Examiner* — Kari K Rodriquez
(74) *Attorney, Agent, or Firm* — Edell, Shapiro & Finnan, LLC

(57) ABSTRACT

An apparatus includes a first and second engaging member to engage a first and second portion of a body toward an upper and lower portion of a back, and a plurality of assemblies connecting the first and second engaging members to maintain a distance between bones of a body portion comprising an area of the back, wherein the body portion resides between the first and second portions, and wherein each assembly comprises a plurality of rods coupling the first engaging member and the second engaging member, and a coupling tube with a first rod of the plurality of rods secured to a proximal end and a second rod of the plurality of rods secured to a distal end, wherein rotation of the coupling tube adjusts a gap between the first and second rods in the coupling tube to control the distance between the bones of the body portion.

14 Claims, 15 Drawing Sheets

(56) References Cited

U.S. PATENT DOCUMENTS

| | | | |
|---|---|---|---|
| 5,405,313 A * | 4/1995 | Albin | A61F 5/026 |
| | | | 602/5 |
| 5,624,387 A | 4/1997 | McGuinness | |
| 5,669,873 A | 9/1997 | Towsley | |
| 6,764,458 B2 | 7/2004 | Polonchek | |
| 8,870,802 B1 | 10/2014 | Anderson et al. | |
| 9,433,814 B2 | 9/2016 | von Hoffmann et al. | |
| 12,496,210 B2 | 12/2025 | Vossoughi | |
| 2010/0262057 A1 | 10/2010 | Chandrasekar et al. | |
| 2016/0175180 A1 | 6/2016 | Bond | |
| 2020/0001135 A1 | 1/2020 | Rajagopal | |
| 2025/0107913 A1 | 4/2025 | Vossoughi | |
| 2025/0107915 A1 | 4/2025 | Vossoughi | |
| 2025/0107916 A1 | 4/2025 | Vossoughi | |

* cited by examiner

100

700

METHOD AND APPARATUS TO MAINTAIN DISTANCE BETWEEN BONES OF A BACK FOR PAIN RELIEF

BACKGROUND

1. Technical Field

Present invention embodiments relate generally to medical devices, and more specifically, to devices that maintain a distance between bones of a joint to prevent bone-on bone-contact and to relieve pain.

2. Discussion of the Related Art

In humans, the knee is a synovial joint that joins the thigh with the lower leg and includes two joints, a tibiofemoral joint between the femur and tibia, and a patellofemoral joint between the femur and patella. As a modified hinge joint, the knee enables a leg to perform both flexion (i.e., a bending moment that decreases the angle of the joint) and extension (i.e., a bending moment that increases the angle of the joint); additionally, the knee permits a small amount of internal as well as external rotation.

Due to the bipedal nature of humans, the knee can be subject to forces that can expose the knee to injury and/or present a source of pain. Knee pain and/or injury is generally caused by the compressive contact forces of the ends of bones making contact with each other. As the protective cartilage wears away, bone-on-bone contact can occur which can be extremely painful.

SUMMARY

According to one embodiment of the present invention, an apparatus includes a first engaging member to engage a first portion of a body toward an upper portion of a back, a second engaging member to engage a second portion of the body toward a lower portion of the back, and a plurality of assemblies connecting the first engaging member and the second engaging member to maintain a distance between bones of a body portion comprising an area of the back, wherein the body portion resides between the first and second portions, and wherein each assembly comprises a plurality of rods coupling the first engaging member and the second engaging member, and a coupling tube with a first rod of the plurality of rods secured to a proximal end and a second rod of the plurality of rods secured to a distal end, wherein rotation of the coupling tube adjusts a gap between the first and second rods in the coupling tube to control the distance between the bones of the body portion. A method of using the apparatus is also provided.

BRIEF DESCRIPTION OF THE DRAWINGS

Generally, like reference numerals in the various figures are utilized to designate like components.

DETAILED DESCRIPTION

Figure 1:
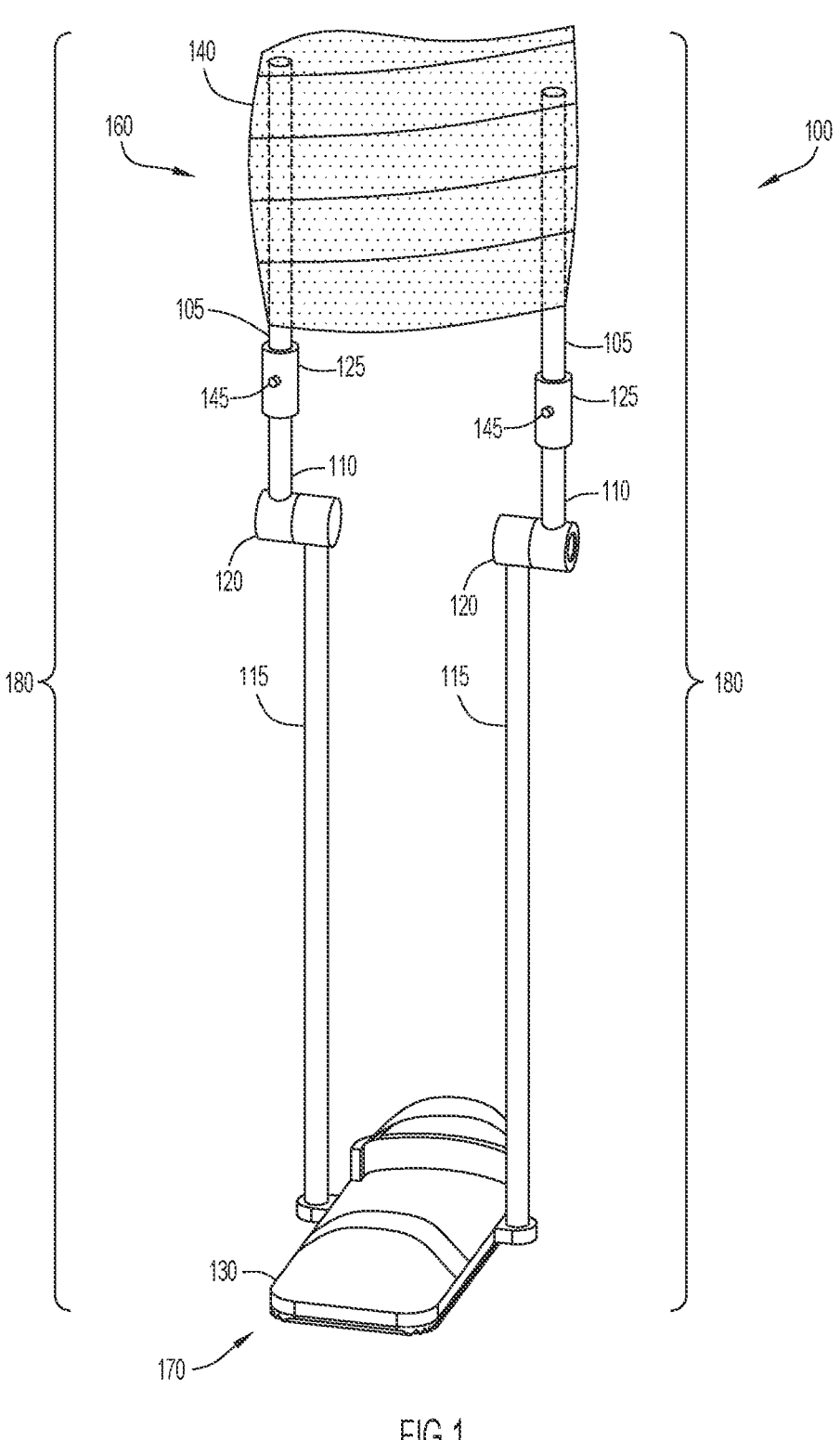
FIG. 1 is a view in perspective of an assembly to maintain a distance between bones of a knee in accordance with an embodiment of the present invention.

Present invention embodiments relate generally to medical devices, and more specifically, to devices that mitigate pain by maintaining a distance between bones. The knee is the largest and most complex joint in the body, containing the distal end of the femur (called the femoral condyle) and the proximal end of the tibia (called the tibial plateau). In usual activities, the femoral condyles glide smoothly on the tibial plateau in a smooth and painless manner, unless there is some sort of knee damage. Knee damage can be caused by trauma, misalignment, and degeneration as well as by conditions like arthritis.

The most common cause of knee pain is osteoarthritis, which is a degenerative disease of the bones of the knee. In osteoarthritis, the naturally-smooth surfaces of the femoral condyle and tibial plateau become damaged and the surfaces roughen over time. This roughness of the surfaces can cause patients to experience continuous pain even from normal walking activities. Since the process can be caused by tissue inflammation, an anti-inflammatory drug and/or therapy are often prescribed. If treating the inflammation fails, then total knee replacement (TKR) surgery may be the only remaining treatment option.

TKR involves the replacement of weight-bearing surfaces of the knee joint with metal or other components. TKR, also known as knee arthroplasty, has become one of the most common orthopedic procedures performed on elderly persons. Initially, TKR procedures were primarily performed on patients over 65 years of age, but recently many patients aged 45 years or older have become candidates for TKR. Painful knees are often the result of wear-and-tear (e.g., aging), sport injuries, accidents, trauma, and even obesity. Accordingly, TKR may also be performed to treat advanced rheumatoid arthritis, psoriatic arthritis, trauma, and/or other painful knee conditions.

Although TKR is a routine surgery, conventional solutions face various problems and limitations. In particular, not all patients are candidates for TKR; for example, many elderly patients are not candidates for TKR. Before a TKR surgery, patients may undergo a variety of alternative treatment, including physical therapy (which is often ineffective), and/or other conservative therapies (such as administering nonsteroidal anti-inflammatory drugs (NSAIDs) or other medications for as many as six months or more). Meanwhile, a patient may suffer serious knee pain while awaiting a TKR procedure. Also, some patients may have other serious disorders that prevent them from undergoing TKR surgery, and thus have no choice but to tolerate the pain. Additionally, some patients must wait until other disorders are first treated. It should be noted that the knee pain can be continuous and not necessarily limited to walking; subjects with knee pain may also feel pain while lying in bed, for example.

Patients who are not candidates for TKR may include those whose knee symptoms are not related to joint disease, patients too overweight for artificial knees to support themselves, those with fragile skin that may adequately protect an operated knee, patients with, or who are prone to, severe infections, patients with unrelated severe illnesses, very old and/or weak patients who cannot tolerate the surgery, and patients having a terminal illness.

Knee pain is commonly generated by a compressive contact force initiated by the two ends of the damaged bones pushing against each other (e.g., bone-on-bone contact). Accordingly, present invention embodiments reduce or substantially eliminate knee pain and/or damage by preventing or reducing compression in the knee. In particular, by separating the damaged ends of the bones by a small distance (e.g., a millimeter or two), the compressive contact force can be substantially eliminated, thereby reducing pain experienced by a patient. Present invention embodiments may accomplish this by providing a device with a first member that attaches to, or otherwise integrates with, a shoe or a patient's foot, and a second member that secures to a thigh. The second member may be in the form of a wrap that wraps around the thigh (e.g., in the shape of a funnel), or adjustable bands or rings that surround and engage the thigh. The first and second members may be connected to each other using a hinge system or similar mechanism to permit movement of the user (e.g., during flexion and/or extension of the knee).

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 2:
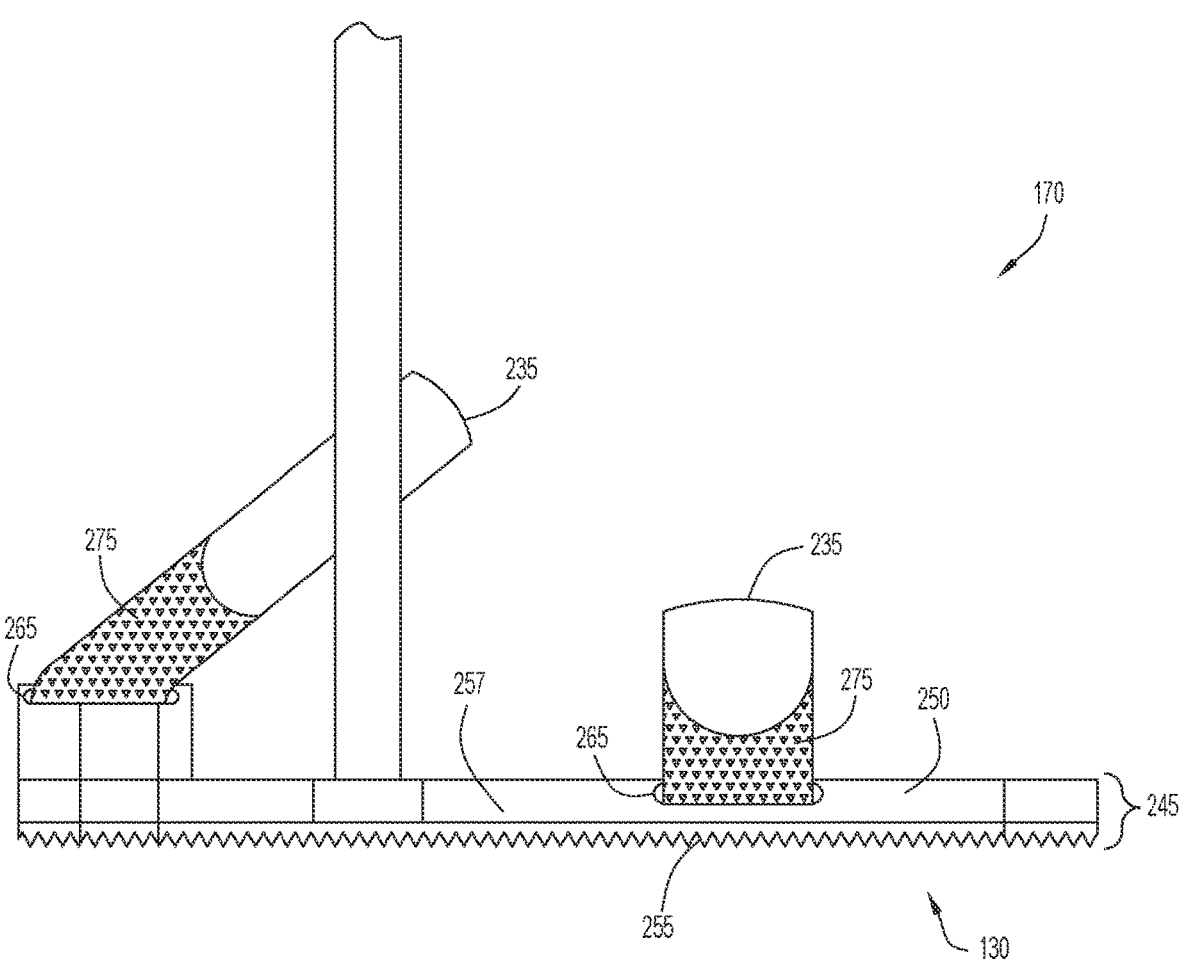
FIG. 2 is a view in perspective of the footplate of the assembly of FIG. 1 in accordance with an embodiment of the present invention.
Figure 3:
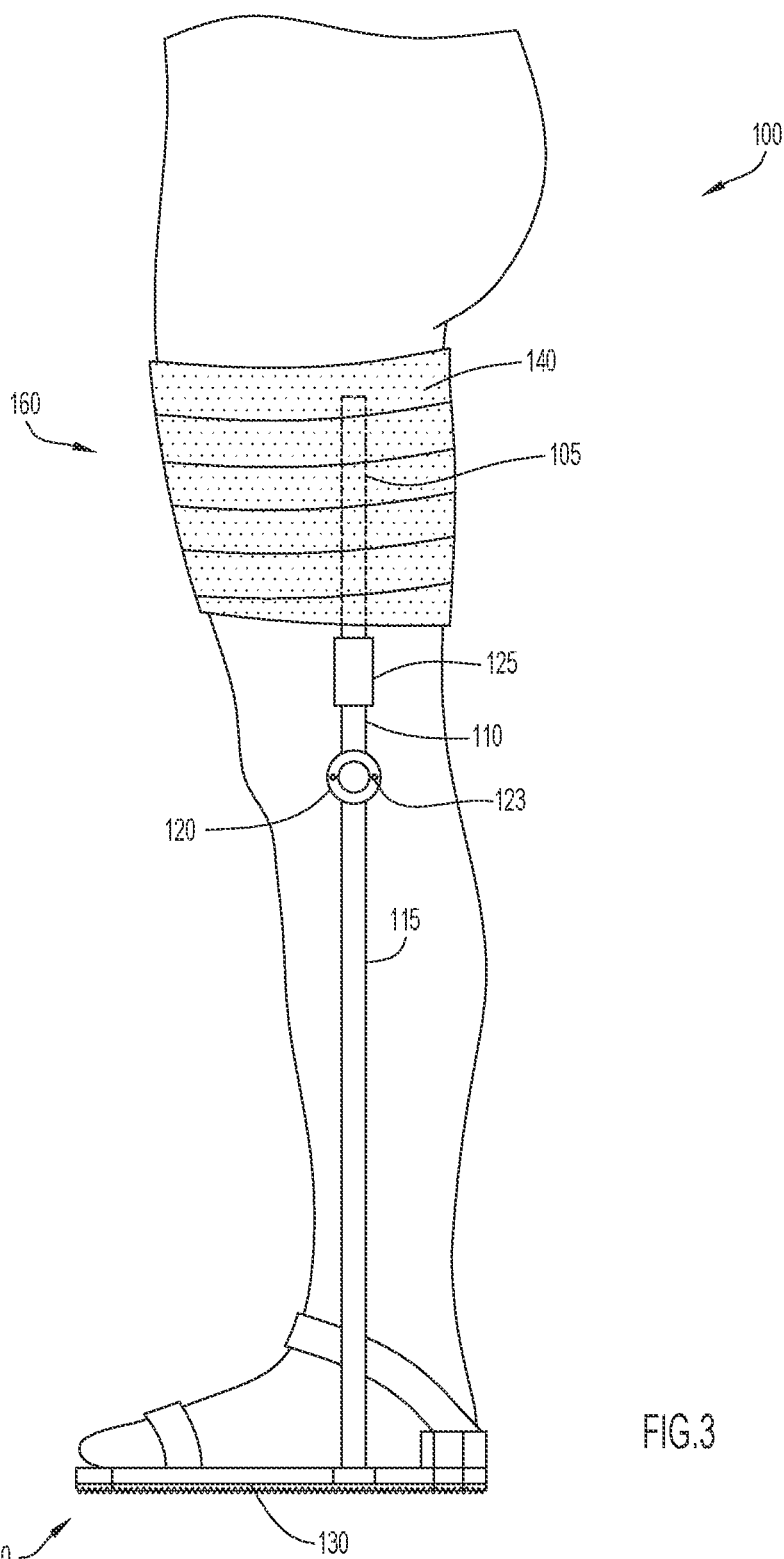
FIG. 3 is a side view in elevation of the assembly of FIG. 1 in accordance with an embodiment of the present invention.

Present invention embodiments will now be described in detail with reference to the Figures. An assembly, device, or apparatus 100 to maintain a distance between bones of a knee for pain relief in accordance with an embodiment of the present invention is illustrated in FIGS. 1-3. Specifically, assembly 100 includes a body engaging member 160, a base member 170, and hinged assemblies 180 connecting the body engaging member and the base member. Hinged assemblies 180 each include an adjustable length to control elongation or stretching of a leg and a distance maintained between bones of a knee as described below.

Body engaging member 160 is preferably in the form of a fabric wrap 140. The fabric wrap typically includes a funnel shape having a proximal portion with greater cross-sectional dimensions than the distal portion to securely attach assembly 100 to a user thigh or other body part. Fabric wrap 140 may be composed of a material that is typically used to attach a prosthetic limb to a user, such as an elastic bandage or similar fabric. In some embodiments, a portion of fabric wrap 140 is provided with a hook-and-loop fastener to enable fabric wrap 140 to be removably attached to itself at a desired tightness around the user leg to prevent or minimize movement of the fabric wrap along the user leg. In addition, fabric wrap 140 may be attached to a user pants and/or belt (e.g., using straps with hook-and-loop fasteners, etc.) to further support the weight of the assembly and prevent slippage or movement along the user leg.

Base member 170 is preferably in the form of a footplate 130 (FIG. 2). Footplate 130 includes a platform 245, straps 235, and a guide or wall portion 250. Footplate 130 may be composed of a material such as metal (e.g., aluminum), a natural or synthetic polymeric material (e.g., plastic), a fiber-reinforced material (e.g., fiberglass), and/or any other suitable material. Platform 245 is generally rectangular or elliptical, and includes dimensions sufficient to receive a user foot or footwear. The platform may include a gripping layer 255 (e.g., rubber, etc.) on a bottom surface to provide a relatively non-slip surface (e.g., for walking, etc.). Guide portion 250 extends upward from the perimeter or edge portions of platform 245 for a slight distance (e.g., at least an inch, etc.) to engage and maintain the user foot on the platform. The height of the guide portion tapers along the side edges of the platform from a platform rear portion toward a platform front portion. The guide portion provides a point of contact for the heel and sides of the user foot or footwear to further secure the user to the footplate. Padding 257 may be disposed on platform 245 to provide comfort to a user. The padding may be constructed of any desired materials (e.g., fabric, foam, etc.).

Straps 235 are attached to the guide portion at corresponding locations along opposing side edges of the platform. A strap 235 may be attached to a respective location on guide portion 250 along a platform side edge and extend across platform 245 to a corresponding location along the other platform side edge. An opening or loop 265 may be attached to, or defined in, guide portion 250 at the corresponding location to receive the strap. The strap may include hook-and-loop fasteners 275 to enable the strap to be inserted through the opening and be secured to itself to provide a desired tightness. The footplate may include any quantity of straps 235 and openings or loops 265 disposed along guide portion 250 at any desired locations. For example, footplate 130 may include a strap 235 disposed toward a front portion of the footplate and another strap 235 disposed toward a rear portion of the footplate. The footplate may alternatively utilize straps that are tied together (e.g., knotted), elastically-taut straps, and/or any other type of straps. In some embodiments, footplate 130 and/or straps 235 are partially or substantially integrated into a footwear item (e.g., a shoe).

Assembly 100 typically includes two substantially parallel hinged assemblies 180 that are connected to wrap 140 and footplate 130 and extend along inner (or medial) and outer (or lateral) exterior portions of a leg. However, the assembly may include any quantity of hinged assemblies arranged in any fashion and extending along any portions of the user leg. Hinged assemblies 180 (FIGS. 1 and 3) are angularly displaced about wrap 140 by approximately one-hundred eighty degrees and extend along inner (or medial) and outer (or lateral) exterior portions of a leg. However, the hinged assemblies may be located at any position relative to each other. Each hinged assembly 180 includes a coupling rod or bar 105, a hinge rod or bar 110, a support rod or bar 115, a hinge 120, and a coupling tube 125. Hinged assemblies 180 each include an adjustable length to control elongation or stretching of a leg and a distance maintained between bones of a knee as described below. The coupling, hinge, and support rods are preferably constructed of fiberglass, but may be constructed of any desired materials (e.g., metal, plastic or polymeric material, a natural material (e.g., wood), etc.). Coupling rod 105 may include a proximal end with any cross-sectional shape (e.g., circular, rectangular, elliptical, triangular, polygonal, etc.), and has a proximal portion attached to interior or exterior surfaces of wrap 140 (for ease of attachment to the fabric wrap, this end can be shaped flat and embedded into the fabric wrap) with a distal portion inserted and attached to a proximal end of coupling tube 125 (this end has a circular cross section with external threads to be engaged with the internal threads in the coupling tube 125). The cross-sectional dimensions of the proximal end of coupling tube 125 are greater than the cross-sectional dimensions of the distal portion of the coupling rod in order to receive the coupling rod (as a threaded attachment).

Hinge rod 110 has a circular cross-sectional shape with external threads on its proximal end to be engaged with the internal threads of the coupling tube 125. The distal end of hinge rod 110 will be rigidly connected to hinge 120. The internal diameter of the coupling tube 125 is greater than the diameter of the hinge rod in order to receive the hinge rod and enable the coupling tube to rotate relative to the threaded hinge rod. The coupling tube is cylindrical, and rotation of the coupling tube enables adjustment of a distance between the coupling and hinge rods via a pin 145 to adjust a length of a corresponding hinged assembly 180 to maintain a distance between bones of the knee as described below. To achieve this, the threads on the two ends of coupling tube 125 have threads of opposing direction, i.e., one end may have clockwise threads and the other end counter-clockwise threads. Similarly, the ends of coupling rod 105 and hinge rod 110 have matching direction external threads to be engaged with the internal threads at the ends of coupling tube 125.

Support rod 115 may include any cross-sectional shape (e.g., circular, rectangular, elliptical, triangular, polygonal, etc.), and has a proximal end connected to hinge 120 with a distal end connected to a rear portion of footplate 130. The hinge is oriented in the direction of knee flexion and extension so that the hinge enables angular movement of hinge rod 110 and support rod 115 to permit flexion and extension of the user knee. Accordingly, coupling rod 105, hinge rod 110, and support rod 115 may be positioned with respect to a user leg in a manner that prevents the user tibia and fibula from compressing against the user femur by maintaining a separation of the tibia and fibular from the femur by a small distance (e.g., 1 mm-2 mm) by providing a small gap at the knee level.

Hinge 120 may include any conventional or other revolute joint that permits one or more degrees of freedom. A degree of freedom of hinge 120 may be oriented in a direction of flexion and extension of the user knee so that hinge 120 may freely permit flexion and extension of the user knee. In some embodiments, hinge 120 is a hinge that is used in a prosthetic limb. In some embodiments, hinge 120 may include one or more stop-pins 123 that are disposed or defined in a hinge interior to prevent rotational or other movement of the hinge, hinge rod 110 and/or support rod 115 beyond a threshold angle (e.g., in order to prevent excessive forward and/or backward flexion of the tibia against the femur).

Figure 4:
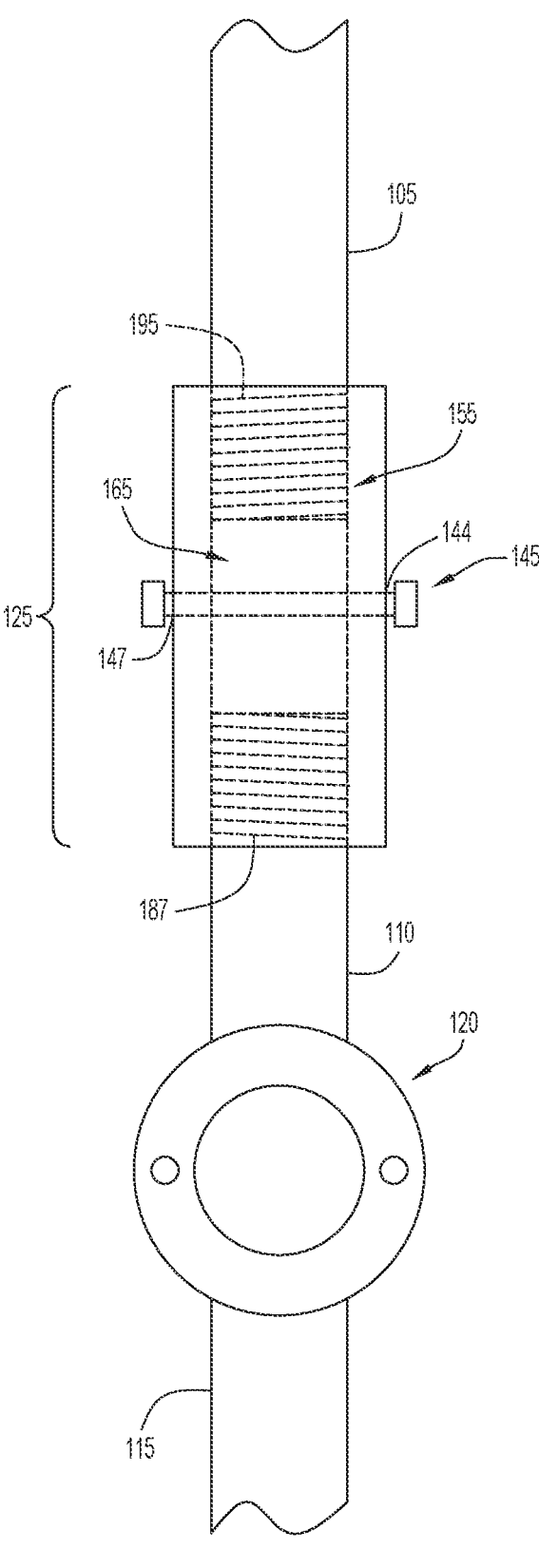
FIG. 4 is a view in elevation of a portion of a hinged assembly of the assembly of FIG. 1 in accordance with an embodiment of the present invention.

Connection of coupling rod 105 and hinge rod 110 to coupling tube 125 in accordance with an embodiment of the present invention is illustrated in FIG. 4. Specifically, coupling tube 125 includes internal threads 155, 187 at both ends, one end has clockwise threads, and the other end has counterclockwise threads defined on an interior surface of a coupling tube.

The depth of an opening space 165 is sufficient enough to prevent the bottom edge of coupling rod 105 and the top edge of hinge rod 110 to touch pin 145 white rotating coupling tube 125.

With reference again to FIG. 4, the rotation of the coupling tube enables adjustment of the length dimension of the gap to control separation of the bones of the knee as described below. As a user walks or otherwise performs flexion and/or extension of the knee, hinge 120 accommodates the knee movement while maintaining separation of the bones of the knee.

Coupling rod 105 includes external threads 195 defined on an exterior surface of a distal portion thereof. Threads 195 of the coupling rod are configured to mate with internal threads 155 defined in the proximal portion of coupling tube 125 to enable the distal end of coupling rod 105 to be attached to the proximal end of coupling tube 125.

Pin 145 may be used to rotate the coupling tube and adjust the space causing separation of the bones. Alternatively, the pin can be eliminated by having a knurled outer surface of the coupling tube. The knurled surface facilitates a non-slip surface for grasping the coupling tube for turning in order to separate the two rods to introduce a gap between the bones.

Assembly 100 can be worn around either of a user's leg such that one hinged assembly 180 is lateral to the user's leg, and another hinged assembly is medial to the user's leg. Assembly 100 may be worn on a left leg of a user, a right leg of a user, or a user may wear a first assembly 100 on one leg and a second assembly 100 on the other leg. In operation, assembly 100 attaches to the user foot and thigh with hinge 120 preferably aligned with the knee. At the foot, footplate 130 goes under the user foot and attaches with straps 235. In some embodiments, footplate 130 may go under a user foot prior to the user donning footwear; that is, footplate 130 may be inserted between the bottom of a user foot and the inside surface of the footwear. At the thigh, fabric wrap 140 wraps around the user thigh. In some embodiments, additional fabric wrap may be provided at other locations, such as the user knee and/or lower leg (e.g., to bind support rod 115 to the user shin).

Once assembly 100 is secured to the user, rotational forces may be applied to pin 145. Applying rotational forces to pin 145 causes coupling tube 125 to freely rotate relative to hinge rod 110 and coupling rod 105 while also engaging threads 155 and 187 to either increase or decrease the amount of insertion of hinge rod 110 and the coupling rod 105 into coupling tube 125, thereby controlling a distance between bones of the knee as described above. Accordingly, assembly 100 can adjust a distance maintained between bones of the knee. The pin basically configures the hinged assemblies with respect to a user leg in a manner that prevents the user's femur compressing against the user's tibia and fibula by maintaining a separation of the tibia and fibula from the femur by a small distance (e.g., 1 mm-2 mm) at the knee level. During walking or other activities, hinge 120 accommodates knee movement (and movement of the hinge and support rods) while maintaining the small distance between the bones of the knee.

Figure 5:
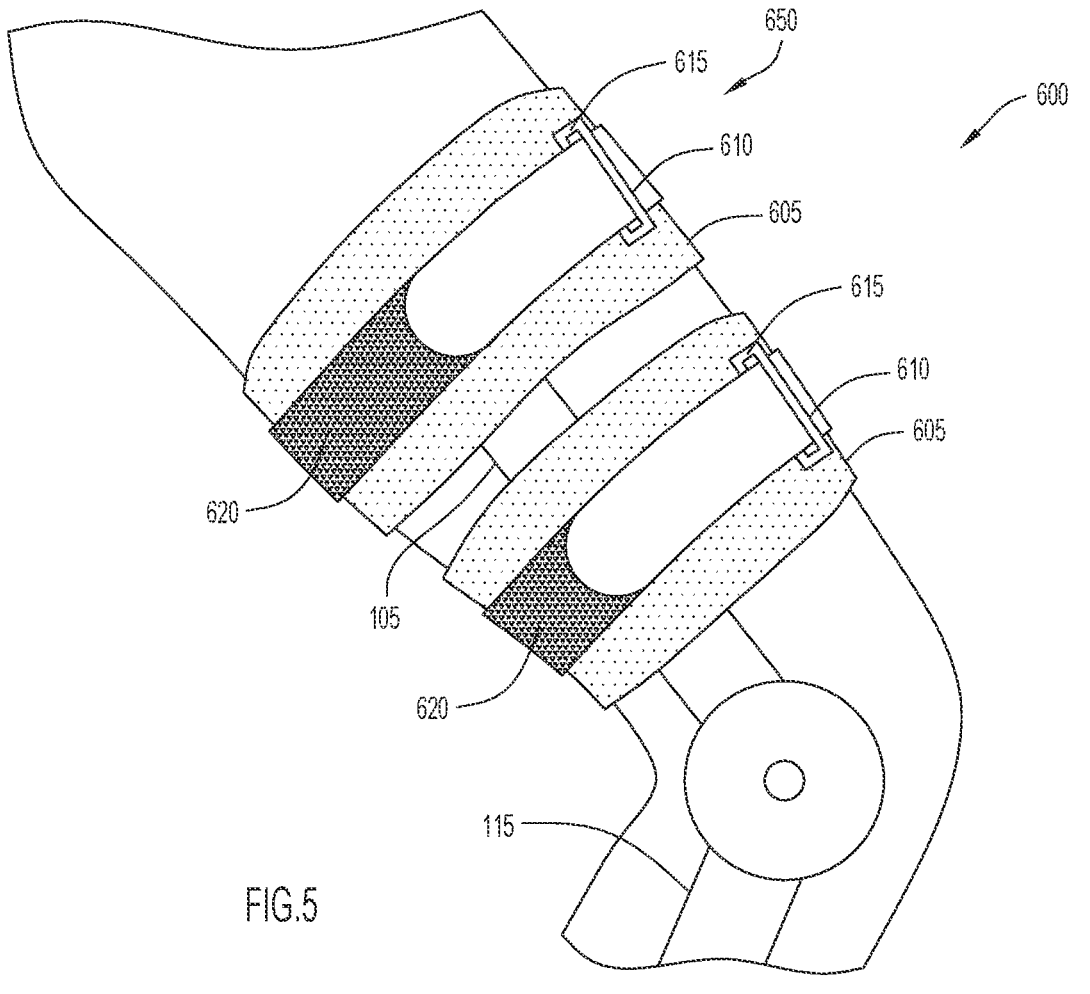
FIG. 5 is a view in perspective of an alternative mechanism for securing the assembly of FIG. 1 to a leg in accordance with an embodiment of the present invention.

An assembly 600 employing an alternative body engaging member in accordance with an embodiment of the present invention is illustrated in FIG. 5. Initially, assembly 600 is substantially similar to assembly 100 described above, except that assembly 600 employs a securing mechanism 650 for body engaging member 160. In particular, securing mechanism 650 includes bands or rings 605 attached to and disposed between coupling rods 105 of hinged assemblies 180. The bands are preferably padded and constructed of fabric, but may be constructed of any suitable materials (e.g., fabric over a flexible base or substrate, etc.). The bands are preferably disposed toward proximal and intermediate portions of coupling rods 105. The bands include overlapping edges that enable opening of the band interior to receive a portion of a user thigh. In order to secure the overlapping ends of the band to retain the thigh, straps 610 are disposed over bands 605. Each strap 610 includes a loop 615 and a hook-and-loop fastener 620. The distal end of strap 610 is inserted through loop 615 to attach the distal portion of the strap to itself via hook-and-loop fastener 620. In this case, the strap may be tightened to a desired tension to secure assembly 600 to the user thigh. The straps may be secured to bands 605 or one or more coupling rods 105.

In operation, assembly 600 receives portions of a user thigh in bands 605, and straps 610 are employed to secure the thigh portions to assembly 600. A user foot is secured in footplate 130 in substantially the same manner described above for assembly 100. Once assembly 600 is secured to the user, rotational forces may be applied to pin 145. Applying rotational forces to pin 145 causes coupling tube 125 to freely rotate relative to hinge rod 110 while also engaging threads 155 to either increase or decrease the amount of insertion of coupling rod 105 into coupling tube 125 to adjust a distance maintained between bones of the knee. Accordingly, assembly 600 can adjust the distance maintained between bones of the knee, and operates in substantially the same manner described above for assembly 100.

Figure 6:
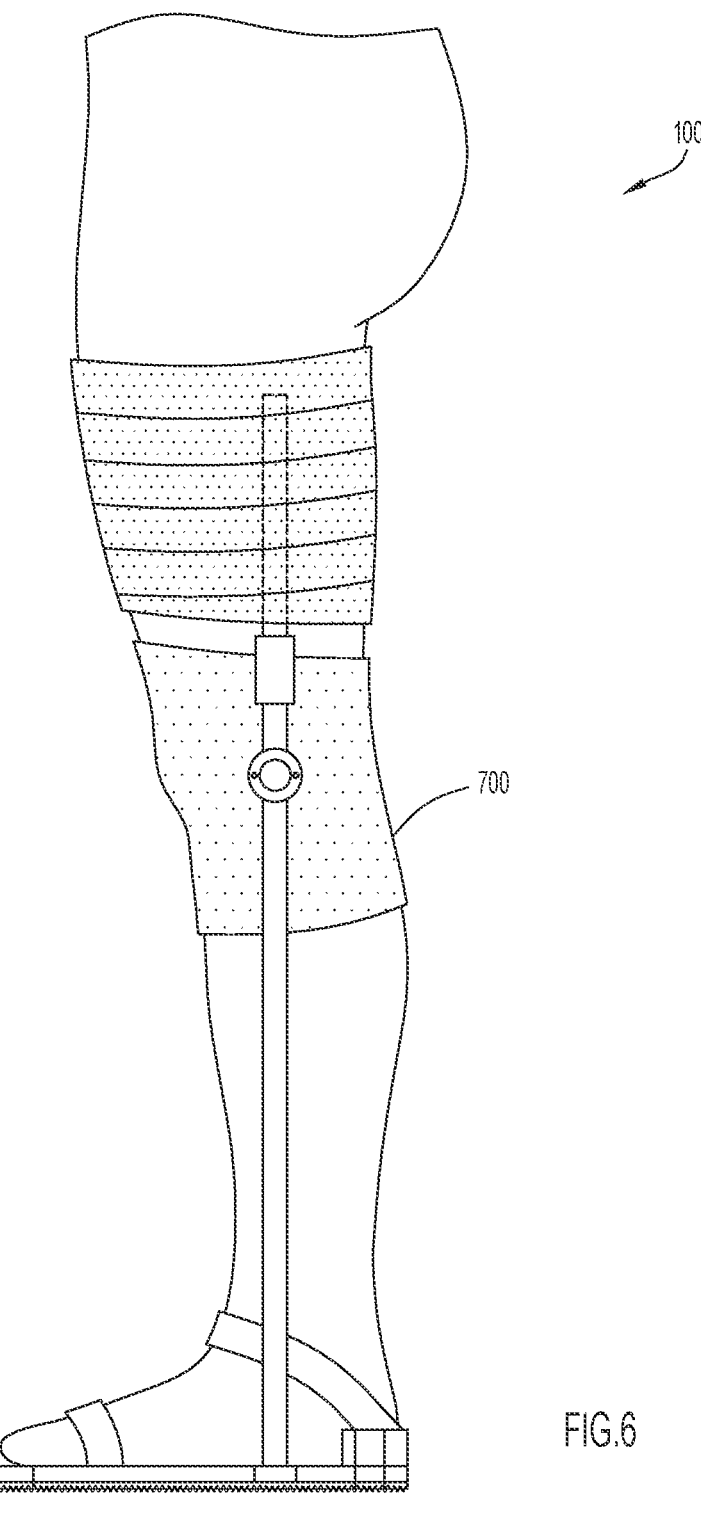
FIG. 6 is a side view in elevation of the assembly of FIG. 1 employed in combination with a knee support or brace in accordance with an embodiment of the present invention.

Assembly 100 may further be employed in combination with other knee devices. By way of example, assembly 100 may be used in combination with a knee support or brace in accordance with an embodiment of the present invention as illustrated in FIG. 6. Conventional knee supports or braces are used to tightly hold the muscles around the knee, and the knee compartment, together to reduce pain and to prevent more knee damage while performing various daily activities, such as walking, running, etc. A user may have employed a conventional or other knee support 700. The knee support is preferably constructed of rubberized stretchable or elastic fabric, and covers portions of a user leg including and surrounding the knee. Once the knee support is secured to the user, assembly 100 may also be secured to the user to separate bones of the knee in substantially the same manner described above. In addition, assembly 600 may be employed by a user with knee support 700 in substantially the same manner described above. Assemblies 100 and 600 may be used in combination with any conventional or other knee supports or braces (e.g., hinged braces, fabric braces, knees taped and/or wrapped, compression or other stockings or wearables, etc.) in substantially the same manner described above.

Figure 7:
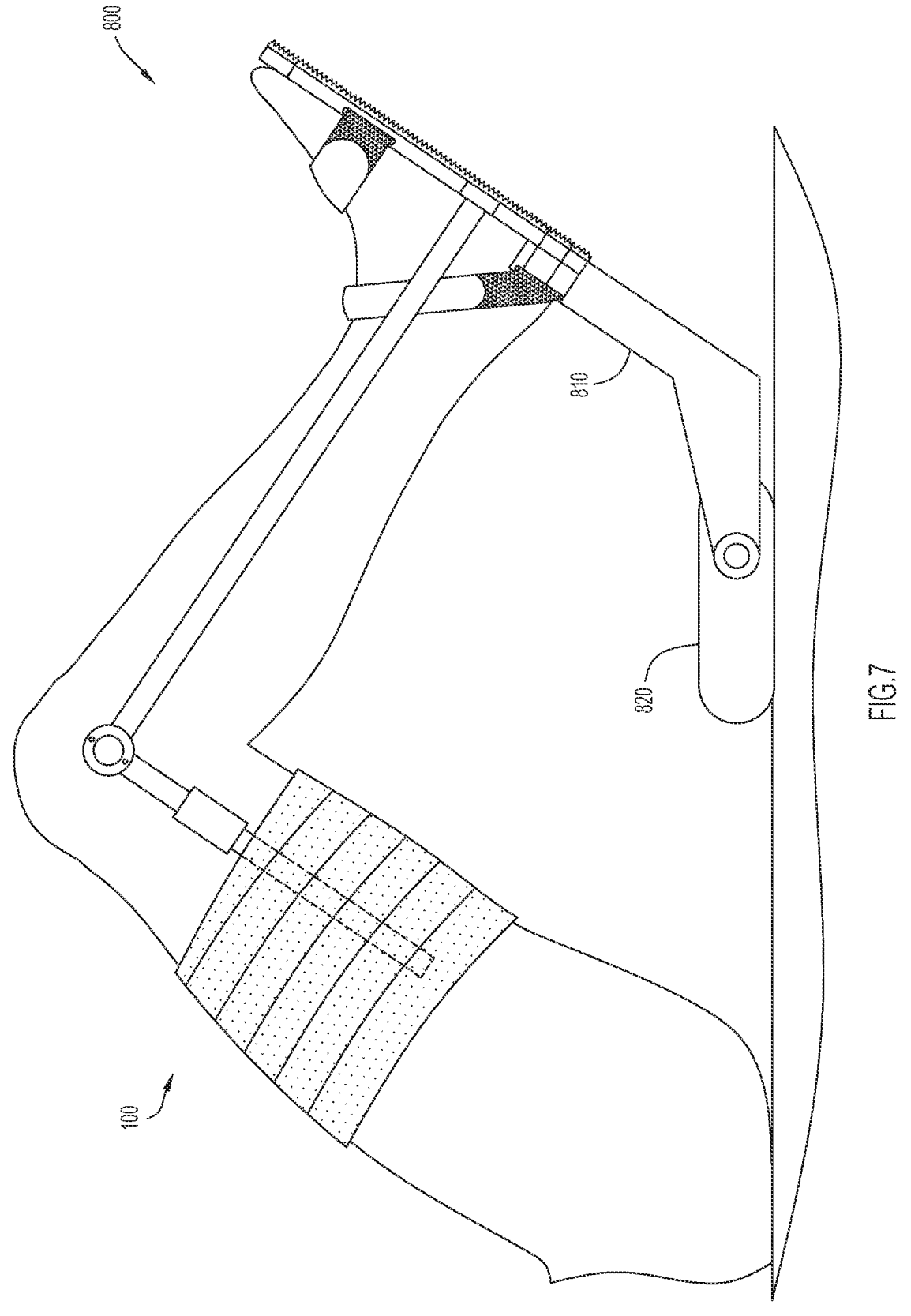
FIG. 7 is a view in perspective of the assembly of FIG. 1 employed in combination with a continuous pressure motion (CPM) device in accordance with an embodiment of the present invention.

By way of further example, assembly 100 may be used in combination with a continuous pressure motion (CPM) device as illustrated in FIG. 7. A CPM device is used in a variety of applications, such as therapy, exercise, increasing knee mobility/flexibility, improving muscle strength, etc. CPM device 800 includes a hinged leg support 810 and a motor 820 that moves the knee through several motions. Assembly 100 may be secured to the user to separate bones of the knee in substantially the same manner described above, and the user may subsequently employ CPM device 800 with the leg having assembly 100 secured thereto. In addition, assembly 600 may be employed by a user for CPM device 800 in substantially the same manner described above.

Present invention embodiments may further be configured to separate bones of various other body parts. For example, an assembly 1000 to maintain a distance between bones of a finger in accordance with an embodiment of the present invention is illustrated in FIGS. 8 and 9.

Figure 8:
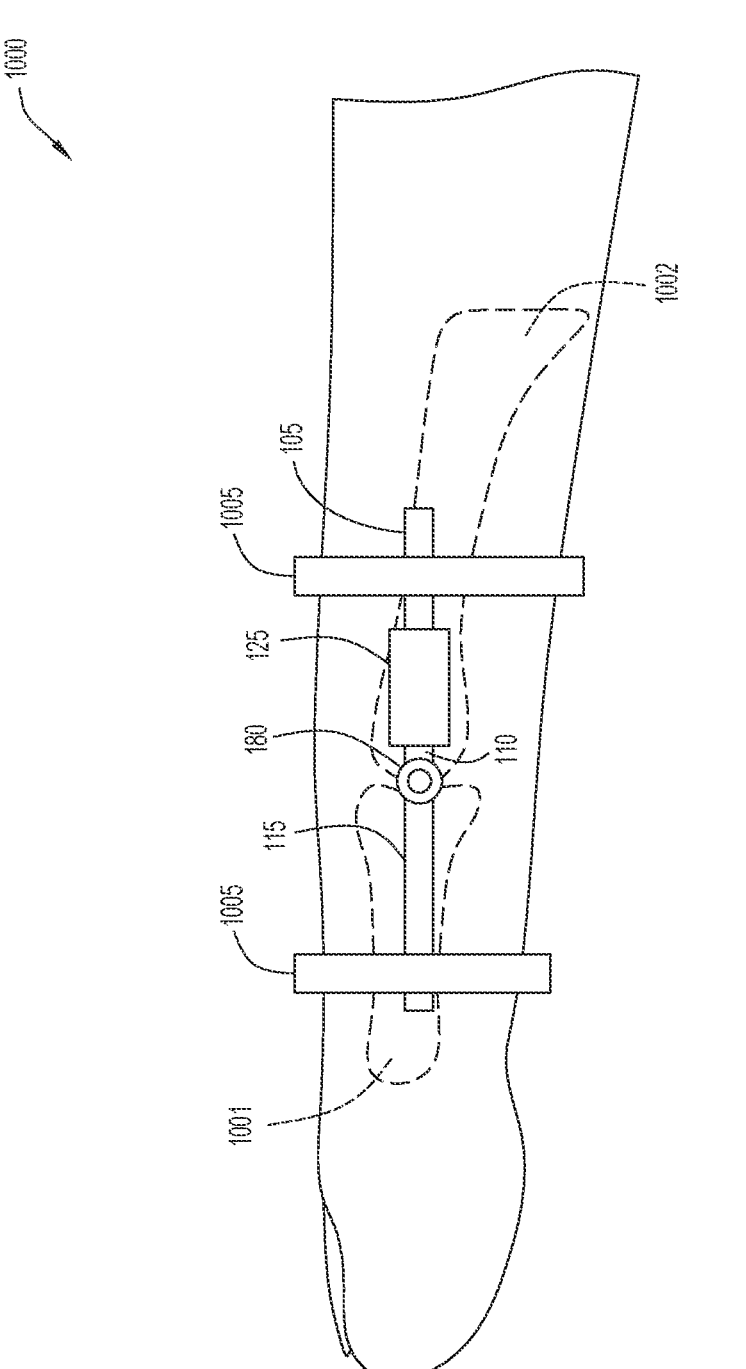
FIG. 8 is a side view in elevation of an assembly to maintain a distance between bones of a finger in accordance with an embodiment of the present invention.
Figure 9:
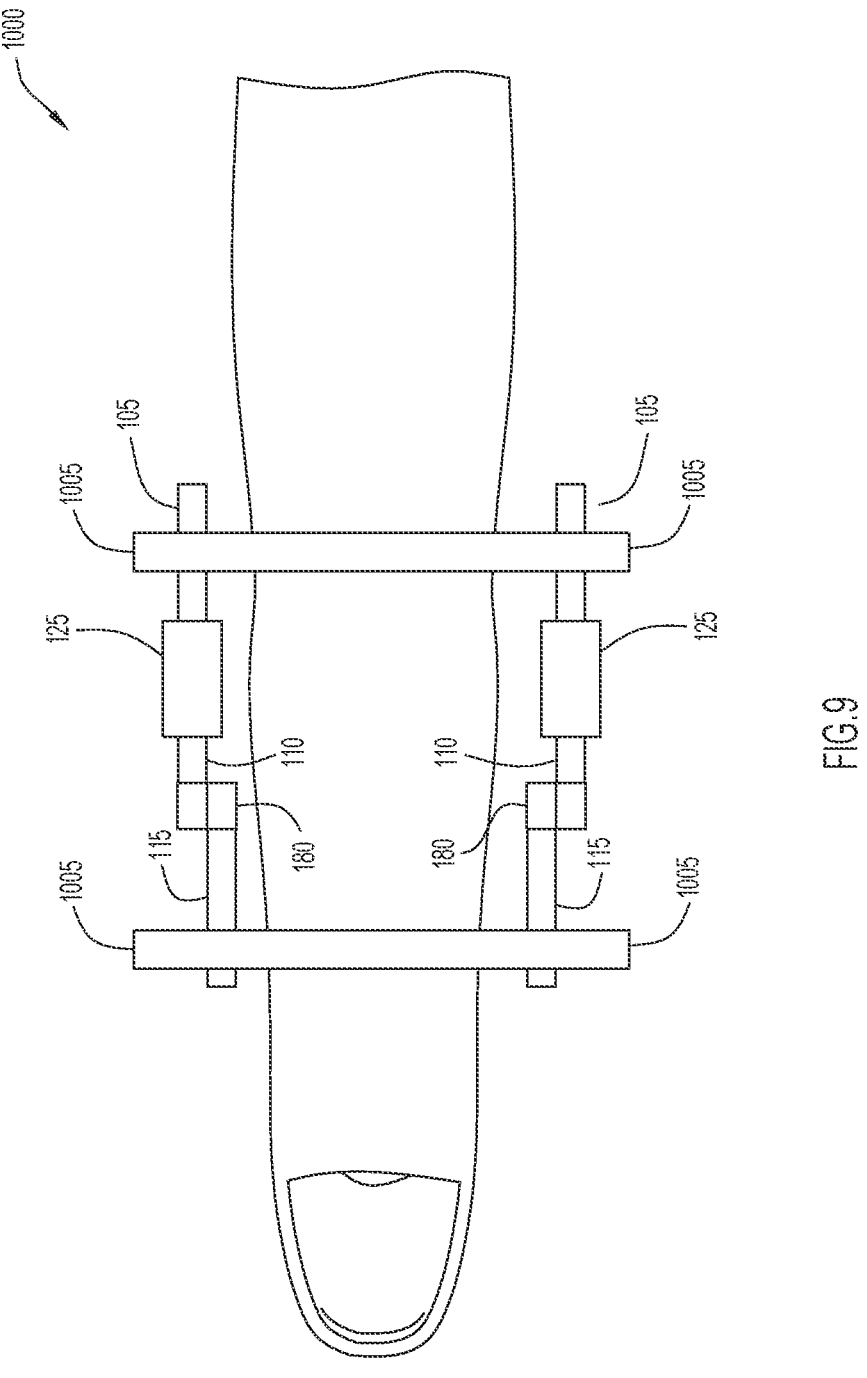
FIG. 9 is a top view of the assembly of FIG. 8 to maintain a distance between bones of a finger in accordance with an embodiment of the present invention.

With reference now to FIGS. 8 and 9, assembly 1000 maintains a distance between bones of a finger in accordance with an embodiment of the present invention. As depicted, the joint that is implicated is a proximal interphalangeal joint, which is between intermediate phalanx 1001 and proximal phalanx 1002. It should be appreciated that assembly 1000 can be provided to other locations of the body, such as the distal interphalangeal joint of a finger, a toe joint, and the like.

Assembly 1000 may be analogous to other embodiments depicted herein, such as assembly 100. As depicted, assembly 1000 includes proximal and distal clamps 1005 and hinged assemblies 180 substantially similar to the hinged assemblies described above and sized for use with a finger. Each clamp 1005 may include a ring-shaped clamp that can be externally attached to the finger at a distance away from the injured joint (e.g., the proximal interphalangeal joint). Clamps 1005 are disposed on opposing sides of the injured joint, and may be tightly secured to the finger to prevent movement of clamps 1005 with respect to the finger once assembly 1000 is provided to the finger. Proximal clamp 1005 is disposed to engage an area toward a base of the finger (or hand palm or interior), while distal clamp 1005 is disposed to engage an area toward a tip of the finger (or toward the fingernail).

In various embodiments, clamps 1005 may be positioned at any location on a user's finger, such as the distal phalanx, the distal interphalangeal joint, the middle phalanx, the proximal interphalangeal joint, the proximal phalanx, the metacarpophalangeal joint, and/or the metacarpal. The clamps 1005 may include a substantially rigid material, such as a metal or plastic, that can be tightly secured to the user's finger by any techniques (e.g., hook and loop fasteners, straps, fabric wrap, friction fit clasps or locks, etc.). In some embodiments, the clamps may include a padding (e.g., polyurethane, polyethylene, etc.) disposed along the interior surface for comfort. In other embodiments, clamps 1005 may be flexible straps or wraps (e.g., similar to wrap 160) that are able to be secured to a user's finger.

Assembly 1000 typically includes two substantially parallel hinged assemblies 180 that are connected to clamps 1005 and extend along inner (or medial) and outer (or lateral) exterior portions of a finger. However, the assembly may include any quantity of hinged assemblies arranged in any fashion and extending between clamps 1005 along any portions of the user finger. Hinged assemblies 180 (FIGS. 8 and 9) are angularly displaced about clamps 1005 by approximately one-hundred eighty degrees and extend along inner (or medial) and outer (or lateral) exterior portions of a finger. However, the hinged assemblies may be located at any position relative to each other. Each hinged assembly 180 includes coupling rod or bar 105, hinge rod or bar 110, support rod or bar 115, hinge 120, and coupling tube 125, each as described above. Hinged assemblies 180 each include an adjustable length to control elongation or stretching of a finger and a distance maintained between bones of a finger in substantially the same manner described above.

Each hinged assembly 180 includes coupling rod 105 having a proximal portion attached to interior or exterior surfaces of a clamp 1005. A distal portion of coupling rod 105 is inserted and attached to a proximal end of coupling tube 125 as described above. Hinge rod 110 has a proximal end connected to a distal end of coupling tube 125, and a distal end connected to hinge 120 as described above. Support rod 115 has a proximal end connected to hinge 120 as described above. A distal end of the support rod is connected to interior or exterior surfaces of a clamp 1005. The cross-sectional dimensions of the distal end of coupling tube 125 are greater than the cross-sectional dimensions of the proximal portion of the hinge rod in order to receive the hinge rod and enable the coupling tube to rotate relative to the hinge rod. The coupling tube is generally cylindrical, and rotation of the coupling tube enables adjustment of a distance between the coupling and hinge rods via pin 145 to adjust a length of a corresponding hinged assembly 180 to maintain a distance between bones of the finger in substantially the same manner described above. The attachment of the coupling tube to coupling rod 105 and hinge rod 110 are similar to the knee apparatus presented earlier, i.e., using right-handed and left-handed threads.

In operation, assembly 1000 attaches to the user finger on opposing sides of an injured/painful joint, preferably with the joint aligned with hinge 120. Once assembly 1000 is secured to the user, rotational forces may be applied to pin 145 of coupling tube 125. Applying rotational forces to pin 145 causes coupling tube 125 to freely rotate relative to hinge rod 110 which either increases or decreases the amount of insertion of coupling rod 105 into coupling tube 125, thereby controlling a distance between bones of the finger as in substantially the same manner described above. Accordingly, assembly 1000 can adjust a distance maintained between bones of the finger. During activities, hinge 120 accommodates finger movement (and movement of the hinge and support rods) while maintaining the small distance between the bones of the finger.

Figure 10A:
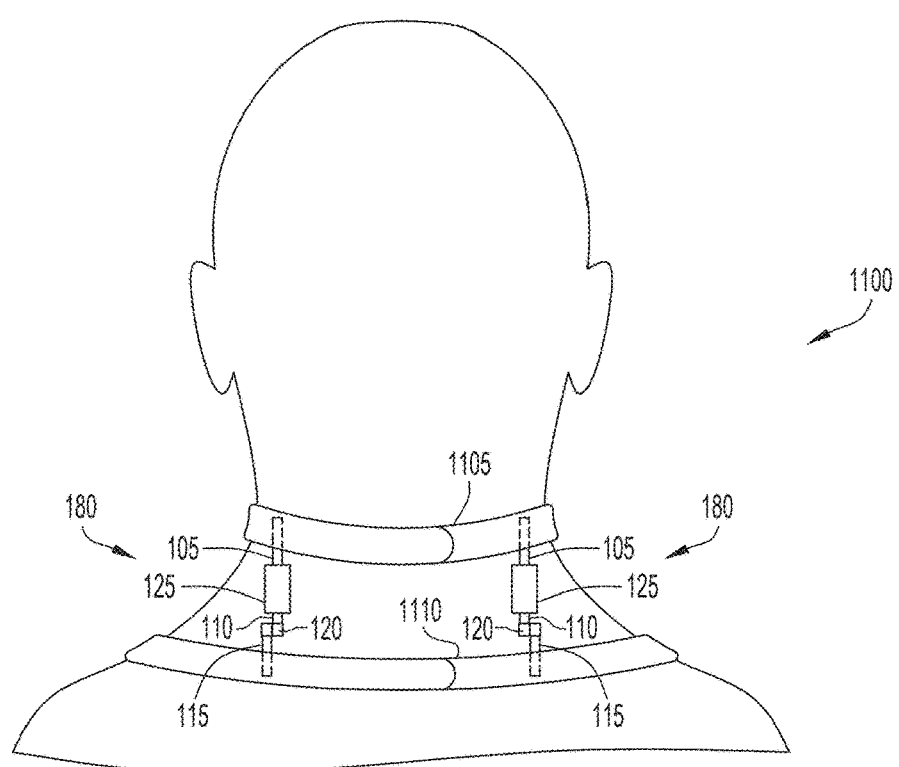
FIGS. 10A and 10B are views in perspective of an assembly to maintain a distance between bones of a neck in accordance with an embodiment of the present invention.
Figure 10B:
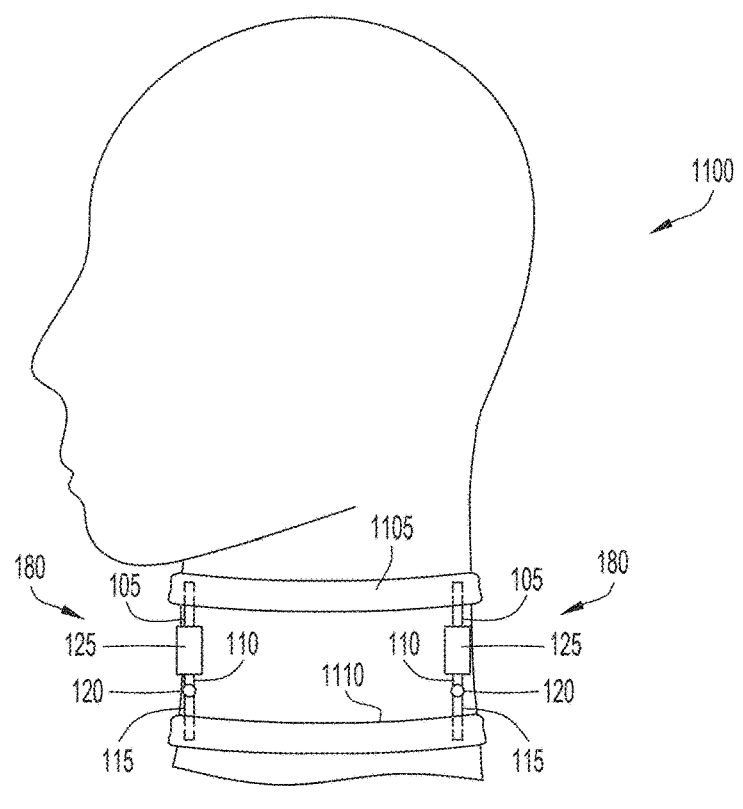

By way of further example, an assembly 1100 to maintain a distance between bones of a neck in accordance with an embodiment of the present invention is illustrated in FIGS. 10A and 10B. As depicted, assembly 1100 includes an upper strap 1105, a lower strap 1110, and a plurality of hinged assemblies 180 substantially similar to the hinged assemblies described above and sized for use with a neck. Upper strap 1105 and lower strap 1110 may include a hook-and-loop fastener or other fastener to secure each strap to itself. Upper strap 1105 and lower strap 1110 may be secured to a user's neck and/or shoulder area above and below an injured or painful joint (e.g., a joint between two cervical vertebrae).

Assembly 1100 typically includes a pair of substantially parallel hinged assemblies 180 that are connected to upper and lower straps 1105, 1110 on opposing sides of a front portion of the neck, and another pair of substantially parallel hinged assemblies 180 that are connected to upper and lower straps 1105, 1110 on opposing sides of a rear portion of the neck. However, the assembly may include any quantity of hinged assemblies arranged in any fashion and extending between the upper and lower straps along any portions of the user neck. Further, the hinged assemblies may be located at any position relative to each other. Each hinged assembly 180 includes coupling rod or bar 105, hinge rod or bar 110, support rod or bar 115, hinge 120, and coupling tube 125, each as described above. Hinged assemblies 180 each include an adjustable length to control elongation or stretching of neck and a distance maintained between bones of a neck in substantially the same manner described above.

Each hinged assembly 180 includes coupling rod 105 having a proximal portion attached to interior or exterior surfaces of upper strap 1105. A distal portion of coupling rod 105 is inserted and attached to a proximal end of coupling tube 125 as described above. Hinge rod 110 has a proximal end connected to a distal end of coupling tube 125, and a distal end connected to hinge 120 as described above. Support rod 115 has a proximal end connected to hinge 120 as described above. A distal end of the support rod is connected to interior or exterior surfaces of lower strap 1110. The cross-sectional dimensions of the distal end of coupling tube 125 are greater than the cross-sectional dimensions of the proximal portion of the hinge rod in order to receive the hinge rod and enable the coupling tube to rotate relative to the hinge rod. The coupling tube is generally cylindrical, and rotation of the coupling tube enables adjustment of a distance between the coupling and hinge rods via pin 145 to adjust a length of a corresponding hinged assembly 180 to maintain a distance between bones of the neck in substantially the same manner described above.

In operation, assembly 1100 attaches to the user. Upper strap 1105 may be positioned to engage an area at any location on an upper portion of a user's neck (e.g., toward the jaw or chin), while lower strap 1110 may be positioned to engage an area at any location toward the lower portion of the user neck and/or on the shoulder area to achieve separation of specific vertebrae, preferably with hinges 120 aligned with the specific vertebrae. Upper strap 1105 and/or lower strap 110 may include any material, such as a fabric wrap, hook-and-loop fastener, and the like. In various embodiments, upper strap 1105 or lower strap 1110 can be positioned on or between any of the atlas (C1), the axis (C2), or the other cervical vertebrae (C3, C4, C5, C6, and C7). Thus, upper strap 1105 or lower strap 1110 may be positioned at a facet joint between an axis and an atlas, a facet joint between an atlas and a first cervical vertebrae, a facet joint between a first cervical vertebrae and a second cervical vertebrae, a facet joint between a second cervical vertebrae and a third cervical vertebrae, a facet joint between a third cervical vertebrae and a fourth cervical vertebrae, a facet joint between a fourth cervical vertebrae and a fifth cervical vertebrae, a facet joint between a fifth cervical vertebrae and a sixth cervical vertebrae, and a facet joint between a sixth cervical vertebrae and a seventh cervical vertebrae.

Once assembly 1100 is secured to the user, rotational forces may be applied to pin 145 of hinge assemblies 180. Applying rotational forces to pin 145 causes coupling tube 125 to freely rotate relative to hinge rod 110 which either increases or decreases the amount of insertion of coupling rod 105 into coupling tube 125, thereby controlling a distance between bones of the neck in substantially the same manner described above. Forces are applied by upper strap 1105 and lower strap 1110 to cause upper strap 1105 and lower strap 1110 to together apply a desired tension force on the user's neck, thereby addressing an injured/painful neck joint. Accordingly, assembly 1100 can adjust a distance maintained between bones of the neck. The pin basically configures the hinged assemblies with respect to a user neck in a manner that prevents the user bones from compressing against each other by maintaining a separation of the bones by a small distance (e.g., 1 mm-2 mm). During activities, hinge 120 accommodates neck movement (and movement of the hinge and support rods) while maintaining the small distance between the bones of the neck.

Figure 11:
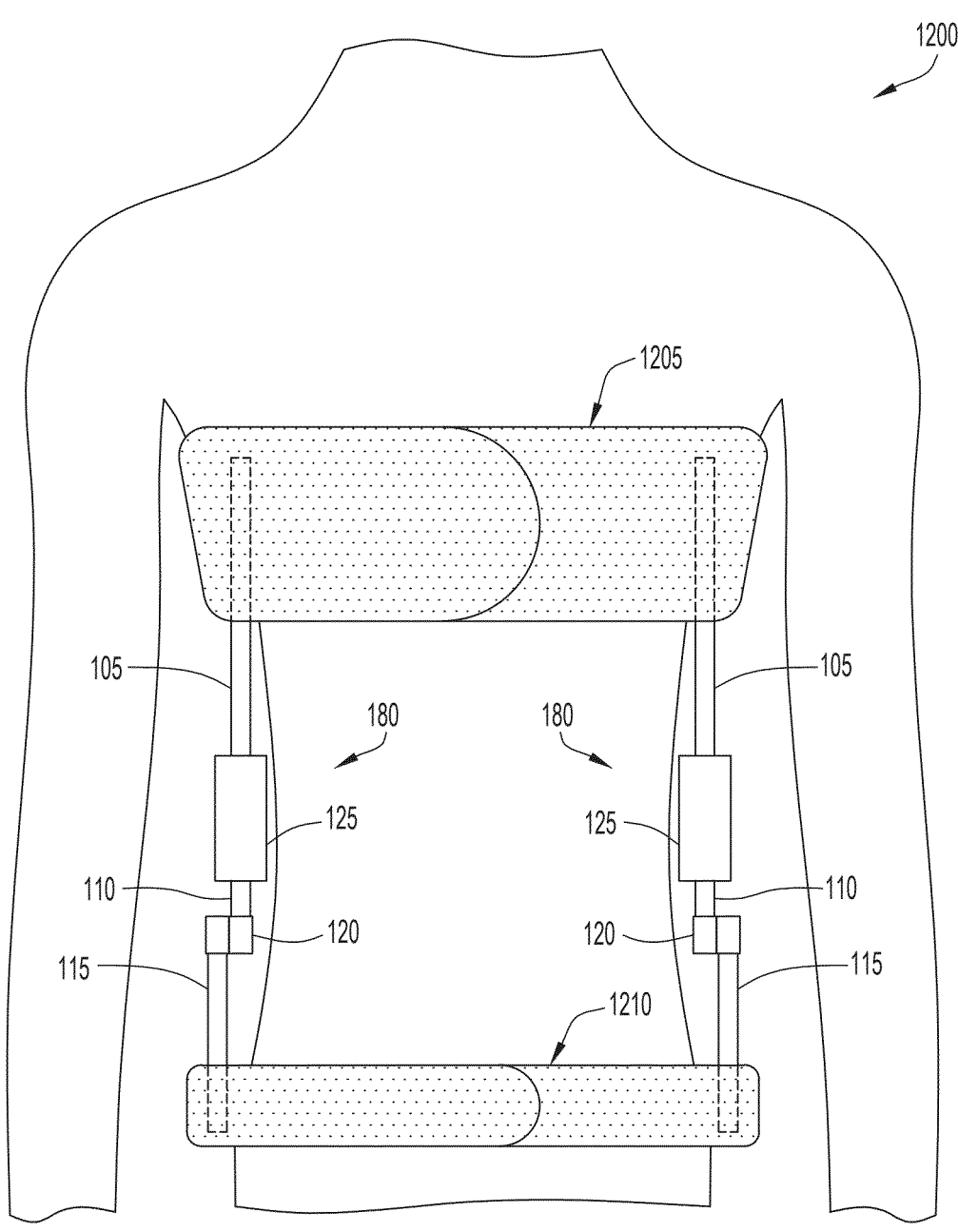
FIG. 11 is a view in perspective of an assembly to maintain a distance between bones of a back in accordance with an embodiment of the present invention.

By way of yet another example, an assembly 1200 to maintain a distance between bones of a back or spine in accordance with an embodiment of the present invention is illustrated in FIG. 11. As depicted, assembly 1200 includes an upper strap or belt 1205, a lower strap or belt 1210, and a plurality of hinged assemblies 180 substantially similar to the hinged assemblies described above and sized for use with a back or spine. Upper strap 1205 and lower strap 1210 may include a hook-and-loop fastener, fabric wrap, or other fastener to secure each strap to itself. Upper strap 1205 and lower strap 1210 may be tightened to a user's torso above and below an injured joint (e.g., a joint between two vertebrae of the back or spine).

Assembly 1200 typically includes two substantially parallel hinged assemblies 180 that are connected to upper strap 1205 and lower strap 1210 and extend along opposing sides of the user torso. However, the assembly may include any quantity of hinged assemblies arranged in any fashion and extending between the upper and lower straps along any portions of the user torso. Hinged assemblies 180 (FIG. 11) are angularly displaced about straps 1205, 1210 by approximately one-hundred eighty degrees and extend along outer (or lateral) exterior portions of a torso. However, the hinged assemblies may be located at any position relative to each other. Each hinged assembly 180 includes coupling rod or bar 105, hinge rod or bar 110, support rod or bar 115, hinge 120, and coupling tube 125, each as described above. Hinged assemblies 180 each include an adjustable length to control elongation or stretching of a back or spine and a distance maintained between bones of a back or spine in substantially the same manner described above.

Each hinged assembly 180 includes coupling rod 105 having a proximal portion attached to interior or exterior surfaces of upper strap 1205. A distal portion of coupling rod 105 is inserted and attached to a proximal end of coupling tube 125 as described above. Hinge rod 110 has a proximal end connected to a distal end of coupling tube 125, and a distal end connected to hinge 120 as described above. Support rod 115 has a proximal end connected to hinge 120 as described above. A distal end of the support rod is connected to interior or exterior surfaces of lower strap 1210. The cross-sectional dimensions of the distal end of coupling tube 125 are greater than the cross-sectional dimensions of the proximal portion of the hinge rod in order to receive the hinge rod and enable the coupling tube to rotate relative to the hinge rod. The coupling tube is generally cylindrical, and rotation of the coupling tube enables adjustment of a distance between the coupling and hinge rods via pin 145 to adjust a length of a corresponding hinged assembly 180 to maintain a distance between bones of the back or spine in substantially the same manner described above.

In operation, assembly 1200 attaches to the user torso on opposing sides of an injured area of the back or spine, preferably with hinge 120 aligned with the injured area. Upper strap 1205 may be positioned to engage an area at any location along a user's back or spine toward the chest, while lower strap 1210 may be positioned to engage an area at any location along a user's back or spine toward the waist to achieve separation of specific vertebrae. In various embodiments, upper strap 1205 or lower strap 1210 can be positioned on or between any of the thoracic vertebrae (i.e., any of T1 through T12) or lumbar vertebrae (i.e., any of L1 through L5).

Once assembly 1200 is secured to the user, rotational forces may be applied to pin 145 of hinge assemblies 180. Applying rotational forces to pin 145 causes coupling tube 125 to freely rotate relative to hinge rod 110 which either increases or decreases the amount of insertion of coupling rod 105 into coupling tube 125, thereby controlling a distance between bones of the back or spine in substantially the same manner described above. Forces are applied by upper strap 1205 and lower strap 1210 to cause upper strap 1205 and lower strap 1210 to together apply a desired tension force on the user's back or spine, thereby addressing an injured spinal joint. Accordingly, assembly 1200 can adjust a distance maintained between bones of the back or spine. The pin basically configures the hinged assemblies with respect to a user back or spine in a manner that prevents the user bones from compressing against each other by maintaining a separation of the bones by a small distance (e.g., 1 mm-2 mm). During activities, hinge 120 accommodates torso movement (and movement of the hinge and support rods) while maintaining the small distance between the bones of the back or spine.

Figure 12:
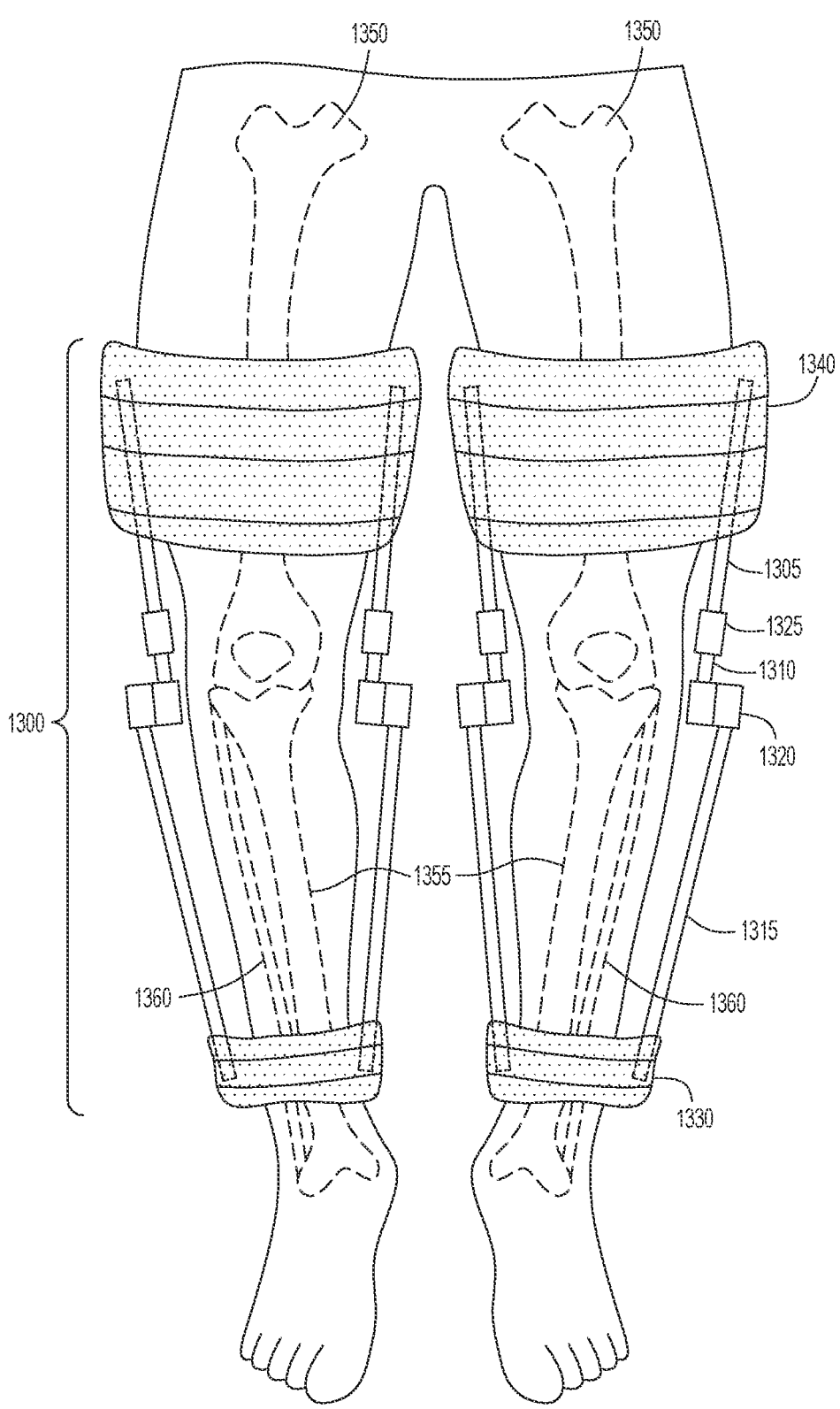
FIG. 12 is a view in perspective of an assembly to rotate bones of a leg in accordance with an embodiment of the present invention.

FIG. 12 is a view in perspective of an assembly 1300 to rotate bones of a leg in accordance with an embodiment of the present invention. As depicted, assembly 1300 includes a coupling rod or bar 1305, a hinge rod or bar 1310, a support rod or bar 1315, a hinge 1320, and a coupling tube 1325 disposed on opposing sides of a user leg. Also depicted are a lower wrap 1330, an upper wrap 1340, and the lower bones of a user's legs, including femurs 1350, tibias 1355, and fibulas 1360. Coupling rod or bar 1305, hinge rod or bar 1310, support rod or bar 1315, hinge 1320, and/or coupling tube 1325 may be substantially similar to coupling rod or bar 105, hinge rod or bar 110, support rod or bar 115, hinge 120, and/or coupling tube 125, respectively, of assembly 100, as depicted and described with reference to FIGS. 1 and 3. Similarly, hinge 1320 may include elements substantially similar to the elements depicted and described with reference to FIG. 4.

Assembly 1300 differs from assembly 100 in that rather than including a footplate (e.g., footplate 130), assembly 1300 includes a lower wrap 1330 in addition to upper wrap 1340. Lower wrap 1330 and/or upper wrap 1340 may be comprised of any suitable material, such as the material used for wrap 140 of assembly 100. By utilizing lower wrap 1330 to retain support rod or bar 1315 near a user's ankle, a torque can be provided by turning coupling tubes 1325 on opposing sides of a user's leg by differing amounts to provide a corresponding moment to the user's leg that causes bones of the leg to be rotated with respect to each other. In particular, by rotating coupling tubes 1325 on opposing sides of a user's leg by differing amounts, the tibia 1355 can be rotated relative to the femur 1350 to correct for a leg misalignment, such as varus or valgus of the leg. In an embodiment, rotating the outer coupling tube 1325 to provide a greater distance than the inner coupling tube, the tibia may be rotated counterclockwise to correct for a varus condition, and rotating the inner coupling tube 1325 to provide a greater distance than the outer coupling tube may cause the tibia to be rotated clockwise to correct for a valgus condition. In various embodiments, assembly 1300 may be worn on one or both legs of a user.

Figure 13:
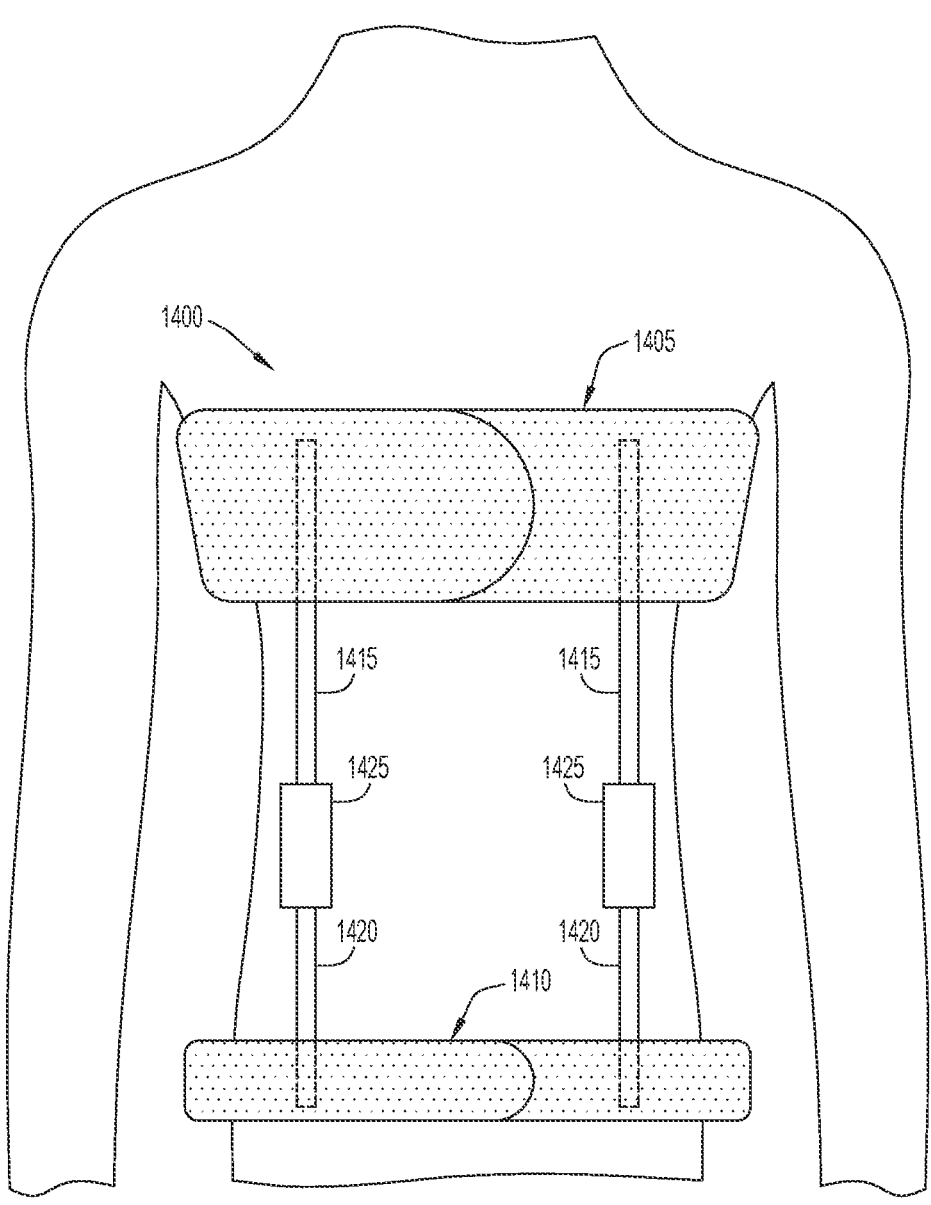
FIG. 13 is a view in perspective of an assembly to rotate bones of a back in accordance with an embodiment of the present invention.

FIG. 13 is a view in perspective of an assembly 1400 to rotate bones of a back in accordance with an embodiment of the present invention. As depicted, assembly 1400 includes a support rod or bar 1420, a coupling rod or bar 1415, a coupling tube 1425, an upper strap or belt 1405, and a lower strap or belt 1410. Coupling rod or bar 1415, support rod or bar 1420, coupling tube 1425, upper strap or belt 1405, and/or lower strap or belt 1410 may be substantially similar to coupling rod or bar 105, support rod or bar 115, coupling tube 125, upper strap or belt 1205, and/or lower strap or belt 1210 respectively, of assembly 1200, as depicted and described with reference to FIG. 11.

Unlike assembly 1200 of FIG. 11, assembly 1400 may not include a hinge or hinge bar, so that the user's back may be retained in a more rigid position during treatment. Moreover, each coupling rod or bar 1415, coupling tube 1425, and support rod or bar 1420 may be positioned more proximal to a user's spine rather than in a distal position. In some embodiments, in order to treat a spinal condition of the upper neck (e.g., involving cervical vertebrae) upper strap or belt 1405 may take a form of the upper portion of a turtleneck shirt in order to provide attachment points for coupling rods or bars 1415.

In some embodiments, two assemblies 1400 may be worn by a user, with one assembly 1400 on the user's front and another assembly 1400 on the user's back. Thus, a total of four coupling rods or bars 1415, coupling tubes 1425, and support rods or bars 1420 may be worn, along with a total of two upper strap or belts 1405 and lower straps or belts 1410. By independently adjusting each of the four coupling tubes 1425 to provide varying distances (in substantially the same manner described above for FIG. 12), a desired position can be achieved to rotate a user's spine in order to treat various conditions relating to spinal curvature, including lordosis, kyphosis, scoliosis, camptocormia, and/or flat back.

Figure 14A:
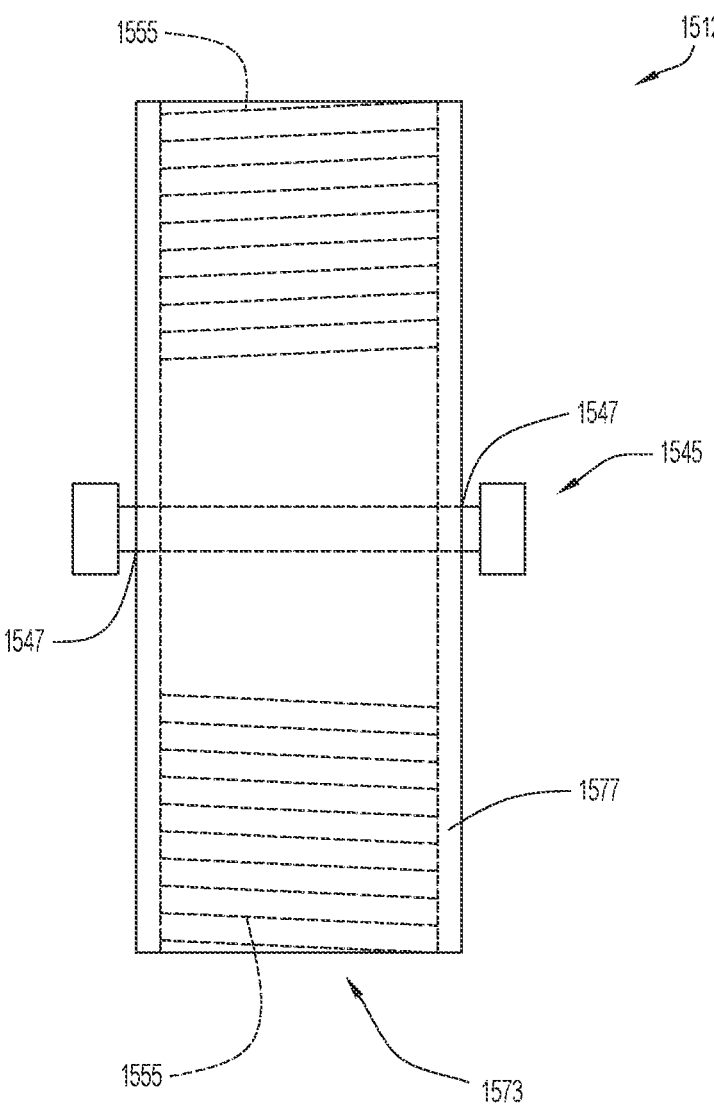
FIG. 14A is a view in partial section of a coupling tube for the assemblies depicted herein in accordance with an embodiment of the present invention.

FIG. 14A is a view in partial section of a coupling tube 1512 for the assemblies depicted herein in accordance with an embodiment of the present invention. Coupling tube 1512 may be utilized in any of the embodiments presented herein, and may correspond to coupling tube 125, coupling tube 1325 and/or coupling tube 1425, as depicted and described with reference to FIGS. 1, 12 and 13, respectively. In contrast to coupling tube 125, which is depicted and described with reference to FIG. 4, coupling tube 1512 includes internal threading 1555 at both end portions. Threading 1555 preferably has different orientations at the different end portions of coupling tube 1512, one end portion includes right-handed threading and the other end portion includes left-handed threading, with the same matching threads on the mating parts.

Coupling tube 1512 includes threads 1555 defined on an interior surface of coupling tube 1512 to engage rods or bars (e.g., coupling rod 105, hinge rod or bar 110, support rods or bars 1415, support rods or bars 1515, coupling rod or bar 1420, and/or coupling rod or bar 1520). Coupling tube 1512 includes openings 1547 to receive pin 1545 that passes through coupling tube 1512, which can facilitate rotation of coupling tube 1512. Coupling tube 1512 is hollow and includes a cavity 1573 disposed therethrough to receive rod or bars (e.g., coupling rod 105, hinge rod or bar 110, support rods or bars 1415, support rods or bars 1515, coupling rod or bar 1420, and/or coupling rod or bar 1520). Cavity 1573 is defined by side walls 1577. Cavity 1573 includes cross-sectional dimensions slightly greater than the cross-sectional dimensions of any corresponding rod or tube so that threading 1555 may engage with a correspondingly-threaded rod or tube.

Figure 14B:
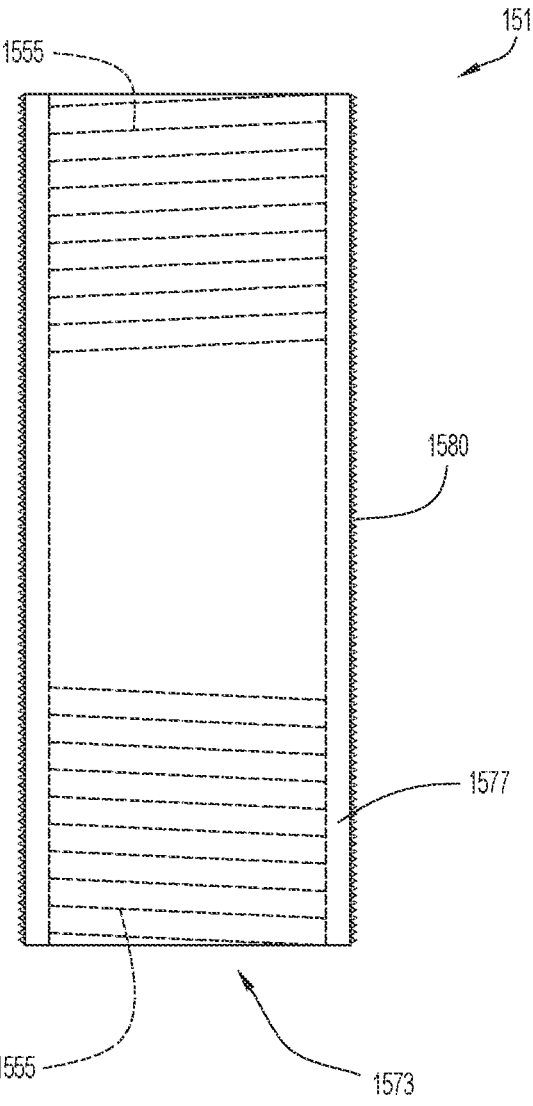
FIG. 14B is a view in partial section of a coupling tube for the assemblies depicted herein in accordance with an embodiment of the present invention.

FIG. 14B is a sectional view of a coupling tube 1513 for the assemblies depicted herein in accordance with an embodiment of the present invention. Coupling tube 1513 may be utilized in any of the embodiments presented herein, and may correspond to coupling tube 125, coupling tube 1325 and/or coupling tube 1425, as depicted and described with reference to FIGS. 1, 12 and 13, respectively. Coupling tube 1513 is substantially similar to coupling tube 1512 described above with reference to FIG. 14A, except that coupling tube 1513 does not include openings (e.g., openings 1547) for a pin (e.g., pin 1545). Thus, coupling tube 1513 may be rotated by gripping the external surface. Coupling tube 1513 may include a particular texture or other features on the exterior surface, such as knurled or ridged surface 1580, to enable a user to grip coupling tube 1513 with a hand in order to make adjustments (e.g., rotational adjustments of coupling tube 1513).

Accordingly, present invention embodiments provide an adjustable device that can reduce or substantially eliminate compression at a user knee or other body part by providing a small gap between bones of that body part. The gap is achieved by providing a substantially rigid portion of material that thereby resists compression beyond a point, which can be adjusted for a particular user. When wearing the device, a user leg muscles may provide further stability of the device. Present invention embodiments are suitable for any user to avoid further deterioration of the knee or other body part and/or to avoid pain, including patients awaiting a TKR procedure and patients who are not good candidates for TKR. After a TKR procedure, some patients may have one leg that is slightly shorter or longer than the other leg. Conventional approaches to addressing this discrepancy typically involve custom shoes with one having a thicker sole. However, present invention embodiments may address this without the need for custom shoes.

Additional benefits of present invention embodiments include the ability to incorporate a continuous passive motion (CPM) device with an embodiment of the device. A continuous passive motion device is a mechanical device that flexes and extends the user's knee at a particular rate after surgery to speed recovery, decrease pain, decrease bleeding, and/or decrease infection. Accordingly, by incorporating an embodiment of the device with a continuous passive motion (CPM) device, the therapeutic value of a continuous passive motion (CPM) device can be improved by adding the benefit of reducing or substantially eliminating compression at the knee. Similarly, other therapies can benefit from the inclusion of an embodiment of the device, thereby decreasing pain and/or decreasing therapy duration.

Additionally, present embodiments may enable a user to simultaneously wear a knee support or brace in the case that the user has suffered a knee ligament injury. Similarly, present invention embodiments may fit over a user stocking, thus enabling a user to wear compressive stockings (e.g., to prevent or reduce the risk of blood clots) while simultaneously benefitting from reduced knee pain and/or damage.

It should be appreciated that present invention embodiments can be configured to reduce or substantially eliminate compression at joints other than the knee, including, but not limited to, finger, neck, and spine. For example, present embodiments can be provided along a user spine to relieve pain in a user spine resulting from disc deterioration or bulging.

Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

The invention claimed is:

1. An apparatus comprising:

a first engaging member adapted to engage a first portion of a body toward an upper portion of a back;

a second engaging member adapted to engage a second portion of the body toward a lower portion of the back; and a plurality of assemblies connecting the first engaging member and the second engaging member and adapted to separate different bones of a body portion comprising an area of the back that have bone-on-bone contact with each other at a back joint and to maintain a distance between the different bones, wherein the body portion resides between the first and second portions, and wherein each assembly comprises:

a plurality of rods coupling the first engaging member and the second engaging member;

a coupling tube with a first rod of the plurality of rods directly secured to each of the first engaging member and a proximal end of the coupling tube and a second rod of the plurality of rods directly secured to a distal end of the coupling tube; and a hinge adapted to be disposed along the plurality of rods at a position aligned with a back joint of a user between vertebrae, wherein the second rod of the plurality of rods is directly secured to a proximal end of the hinge and a third rod of the plurality of rods is directly secured to each of a distal end of the hinge and the second engaging member, wherein the hinge includes a degree of freedom oriented in a direction of movement of a torso of the user and a plurality of stop-pins disposed in a hinge interior defining a threshold angle for rotation of the hinge, wherein the hinge is further adapted to enable angular movement of the second and third rods in accordance with the plurality of stop-pins and maintain the distance between the different bones during the movement of the torso, and wherein the coupling tube of each assembly is rotatable and adapted to adjust a gap between the first and second rods in the coupling tube based on rotation and elongate each assembly and the back to separate and provide the distance between the different bones having bone-on-bone contact with each other.

2. The apparatus of claim 1, wherein the first engaging member or the second engaging member includes a strap adapted to secure the first portion or the second portion of the body.

3. The apparatus of claim 1, wherein the plurality of assemblies is adapted to separate two bones selected from a group of: thoracic vertebrae, and lumbar vertebrae.

4. The apparatus of claim 1, wherein each assembly further includes a pin disposed through the coupling tube, wherein rotational forces applied to the pin rotate the coupling tube to adjust the gap.

5. The apparatus of claim 1, wherein a first assembly of the plurality of assemblies is adapted to be secured on a first exterior portion of the torso, and wherein a second assembly of the plurality of assemblies is adapted to be secured on an opposing exterior portion of the torso.

6. The apparatus of claim 1, wherein the hinge is adapted to be aligned with the back joint selected from a group of: a joint between two thoracic vertebrae, a joint between a thoracic vertebra and a lumbar vertebra, and a joint between two lumbar vertebrae.

7. The apparatus of claim 1, wherein the second engaging member is further adapted to engage the second portion of the body toward the lower portion of the back along thoracic vertebrae.

8. A method for maintaining a distance between bones of a body portion comprising an area of a back using a device comprising a first engaging member, a second engaging member, and a plurality of assemblies connecting the first engaging member and the second engaging member, wherein each assembly comprises a plurality of rods coupling the first engaging member and the second engaging member, a coupling tube with a first rod of the plurality of rods directly secured to each of the first engaging member and a proximal end of the coupling tube and a second rod of the plurality of rods directly secured to a distal end of the coupling tube, and a hinge adapted to be disposed along the plurality of rods at a position aligned with a back joint of a user between vertebrae, wherein the second rod of the plurality of rods is directly secured to a proximal end of the hinge and a third rod of the plurality of rods is directly secured to each of a distal end of the hinge and the second engaging member, and wherein the hinge includes a degree of freedom oriented in a direction of movement of a torso of the user and a plurality of stop-pins disposed in a hinge interior defining a threshold angle for rotation of the hinge, the method comprising:

engaging a first portion of a body toward an upper portion of the back with the first engaging member of the device;

engaging a second portion of the body toward a lower portion of the back with the second engaging member of the device, wherein the body portion resides between the first and second portions;

separating, and providing a distance between, different bones of the body portion comprising the area of the back that have bone-on-bone contact with each other at a back joint via the device by adjusting a gap between the first and second rods in the coupling tube of each assembly based on rotation of the coupling tube of each assembly that elongates each assembly and the back; and maintaining the distance between the different bones during the movement of the torso by the hinge enabling angular movement of the second and third rods in accordance with the plurality of stop-pins.

9. The method of claim 8, wherein the first engaging member or the second engaging member includes a strap adapted to secure the first portion or the second portion of the body.

10. The method of claim 8, wherein the plurality of assemblies is adapted to separate two bones selected from a group of: thoracic vertebrae, and lumbar vertebrae.

11. The method of claim 8, wherein each assembly further includes a pin disposed through the coupling tube, wherein rotational forces applied to the pin rotate the coupling tube to adjust the gap.

12. The method of claim 8, wherein a first assembly of the plurality of assemblies is secured on a first exterior portion of the torso, and wherein a second assembly of the plurality of assemblies is secured on an opposing portion of the torso.

13. The method of claim 8, wherein the hinge is aligned with the back joint selected from a group of: a joint between two thoracic vertebrae, a joint between a thoracic vertebra and a lumbar vertebra, and a joint between two lumbar vertebrae.

14. The method of claim 8, wherein engaging the second portion of the body toward the lower portion of the back includes:

engaging the second portion of the body toward the lower portion of the back along thoracic vertebrae with the second engaging member of the device.

\* \* \* \* \*